United States Patent [19]
Dreyer, Jr.

[11] Patent Number: 5,258,896
[45] Date of Patent: Nov. 2, 1993

[54] LINE LIGHT SOURCE

[75] Inventor: John F. Dreyer, Jr., North Oaks, Minn.

[73] Assignee: Minnesota Mining and Manufacturing Company, Saint Paul, Minn.

[21] Appl. No.: 893,932

[22] Filed: Jun. 4, 1992

[51] Int. Cl.⁵ .................................... F21V 7/00
[52] U.S. Cl. .................... 362/307; 362/311; 362/309
[58] Field of Search ............... 362/186, 202, 307-309, 362/311

[56] References Cited

U.S. PATENT DOCUMENTS

| | | | |
|---|---|---|---|
| 3,383,675 | 5/1968 | Allardice et al. | 362/186 |
| 4,260,220 | 4/1981 | Whitehead | 350/96.28 |
| 4,615,579 | 10/1986 | Whitehead | 350/96.1 |
| 4,744,013 | 5/1988 | Lee et al. | 362/202 |
| 4,750,798 | 6/1988 | Whitehead | 350/96.10 |
| 4,782,433 | 11/1988 | Rombough | 362/186 |
| 4,787,708 | 11/1988 | Whitehead | 350/96.28 |
| 4,805,984 | 2/1989 | cobb | 350/96.28 |
| 4,834,495 | 5/1989 | Whitehead et al. | 350/96.28 |
| 4,850,665 | 7/1989 | Whitehead | 350/96.10 |
| 4,890,203 | 12/1989 | Watson | 362/202 |
| 4,906,070 | 3/1990 | Cobb | 350/286 |
| 4,912,605 | 3/1990 | Whitehead | 362/32 |
| 4,996,632 | 2/1991 | Aikens | 362/32 |
| 5,016,143 | 5/1991 | Aikens | 362/32 |
| 5,040,883 | 8/1991 | Cobb | 350/452 |
| 5,043,850 | 8/1991 | Dreyer | 362/26 |
| 5,056,892 | 10/1991 | Cobb | 359/831 |

*Primary Examiner*—Carroll B. Dority
*Attorney, Agent, or Firm*—Gary L. Griswold; Walter N. Kirn; Stephen W. Buckingham

[57] ABSTRACT

A line light source has a light-emitting element that emits light into an insertion conduit. A light absorber absorbs light that makes greater than a predetermined angle with the axis of the light conduit.

8 Claims, 2 Drawing Sheets

Distance (m)

LINE LIGHT SOURCE

BACKGROUND OF THE INVENTION

Light sources used in traffic and navigational control are generally point or near-point sources. Common examples are traffic semaphores and hazard lights commonly placed around road construction areas.

More recently line sources have become useful in traffic control applications. One such line source is taught by U.S. Pat. No. 5,043,850 (Dreyer, Jr.), commonly assigned herewith. According to the light source taught by that patent, a light conduit of the type taught by U.S. Pat. No. 4,805,984 (Cobb, Jr.) is utilized. Two lamps, differing in at least one optical property, are positioned in containers called lighthouses such that light is inserted into each end of the light conduit. The light is emitted from the conduit in directions such that the light will appear brightest to a person looking along the conduit. If the optical property that differs is color, a person looking one direction along the conduit will see a different color than a person looking the other direction.

A related type of product is produced when only a single lamp is utilized. When such a structure is constructed, the line source will be visible to a person looking along the light conduit in a direction toward the light source, but will not be readily apparent to a person looking along the light conduit away from the light source.

A problem that arises in such line light sources, both unidirectional and bidirectional, arises from the fact that the light sources utilizing parabolic reflectors are not perfectly collimated. Most of the light wall fall inside a directional cone that is acceptable, but some will be directed outside of that cone. That light outside of the preferred cone, which can be described as highly uncollimated, light will escape the tube very close to the insertion end of the tube. This is because it will undergo significantly more collisions with the walls of the light conduit. With each collision a percentage will escape the conduit and the remainder will be reflected and guided along the tube. In addition, the light emitted within the preferred directional cone will contribute illumination in an amount that is relatively constant over the entire length of the conduit. This will cause the line light source to be very bright at the insertion end and then to be relatively uniform in brightness over the remainder of the tube. A more uniform brightness would be desirable.

SUMMARY OF THE INVENTION

According to the present invention, a line light source has a light-emitting element that emits light into an insertion end of a tubular light conduit. A light absorber absorbs light that makes greater than a predetermined angle with the axis of the light conduit.

DETAILED DESCRIPTION OF A PREFERRED EMBODIMENT

Figure 1:
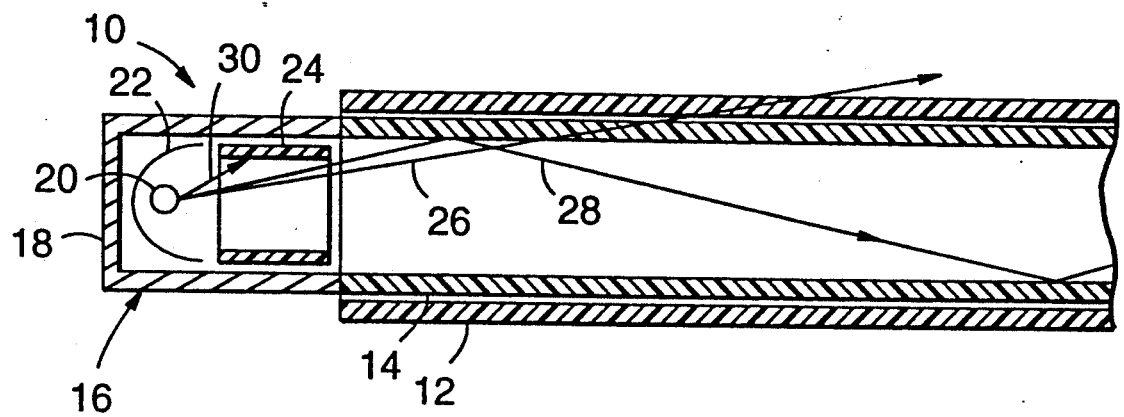
FIG. 1 is a cross-sectional view of a first embodiment of the invention along its axis.

FIG. 1 illustrates one embodiment of the present invention. As shown in FIG. 1, a line light source, designated generally as 10, includes a tube 12 and a structured surface light guide 14 inside tube 12 and a lighthouse 16. Tube 12 is provided to give strength and protection to light guide 14 and may be of any transparent material, typically polycarbonate or an acrylic. Likewise structured surface light guide 14 may be of any appropriate transparent material including acrylics or polycarbonates. Preferably light guide 14 has a plurality of substantially right-angled prisms on its outer surface and a smooth inner surface. A suitable material for making structured surface light conduit 14 is commercially available from Minnesota Mining and Manufacturing Company under the name 3M Optical Lighting Film and is described in U.S. Pat. No. 4,906,070. In a preferred embodiment, light conduit 14 is approximately 10 cm (4 inches) in diameter and 30 m (100 feet) long.

Figure 2:
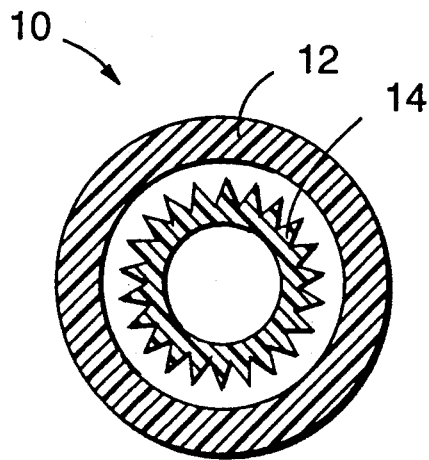
FIG. 2 is a cross-sectional view of the embodiment of FIG. 1 perpendicular to its axis.

FIG. 2 is a cross-sectional view of support tube 12 and light conduit 14 showing that they are preferably circular and concentric. As shown, there is a gap between support tube 12 and light conduit 14, although no such gap is required.

Lighthouse 16 includes a case 18. Case 18 may be of any suitable material, but is preferably of a metal such as aluminum. Inside case 18 is a partially-collimated light source. As shown in FIG. 1, the light source is a lamp 20 with a parabolic reflector 22. Other collimated light sources may be used, however.

The light emitted by bulb 20 is represented by three rays 26, 28, and 30. Light rays 26 and 28 fall within the generally desired directional cone and will be transported along light conduit 14 until they escape. As shown, for example only, light ray 26 escapes on its first contact with light conduit 14 while light ray 28 is shown being reflected by light conduit 14 in order to escape at some location beyond that shown in FIG. 1.

Light ray 30 deviates significantly from the desired directional cone. It is light rays such as ray 30 that cause the undesirable bright regions near the light source in the line light sources of the prior art. In order to eliminate light travelling in such a direction, a light absorber 24 is provided. Light absorber 24 will absorb highly uncollimated light such as light ray 30 leaving only light travelling within the desired directional cone. Effectively light absorber 24 absorbs light travelling in a direction that makes greater than a predetermined angle with the axis of the light conduit.

Absorber 24 may be of any material and color that will absorb the light emitted by bulb 20. If, as is often the case, bulb 20 emits white light, absorber 24 should be flat black. In some tests absorbers of black paper were used successfully. Metallic absorbers painted flat black may also be used. If, however, bulb 20 emits colored light, absorber 24 may be of any color that will absorb light of the color emitted by bulb 20. It is important that light absorber 24 be absorptive, however. If it reflects the light, the bright region will simply be moved farther down the tube.

Figure 4:
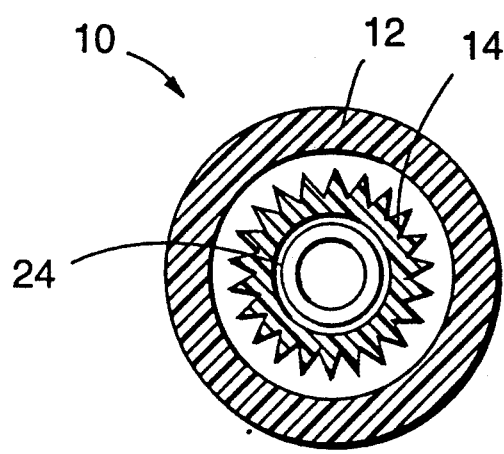
FIG. 4 is a cross sectional view of the embodiment of FIG. 3 perpendicular to its axis.
Figure 3:
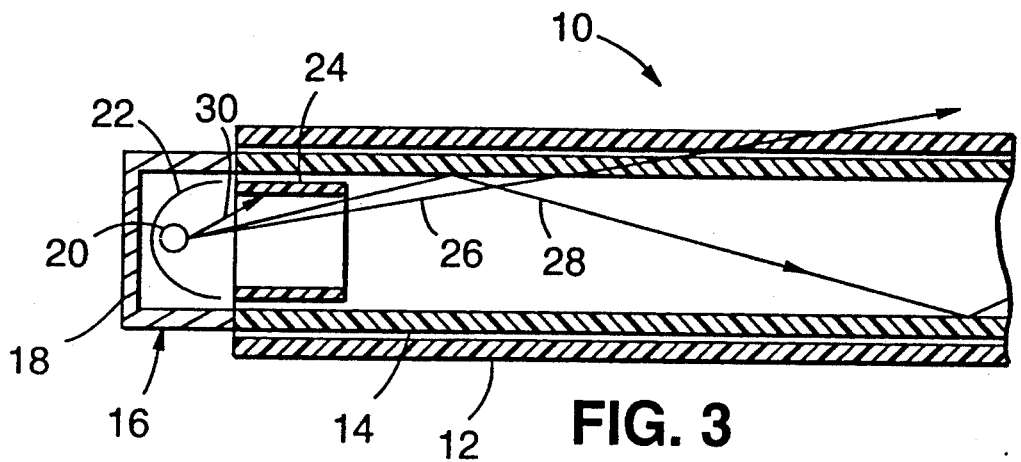
FIG. 3 is a cross-sectional view of a second embodiment of the invention along its axis.

As shown in FIG. 1, absorber 24 is located inside lighthouse 16. Alternatively, lighthouse 16 could be made shorter and absorber 24 placed inside light conduit 14 as shown in FIG. 3. This arrangement is shown in cross section in FIG. 4. If the arrangement of FIG. 3 is used, light absorber 24 must be inside light conduit 14 to prevent light conduit 14 from reflecting the light and conducting it along the tube. As shown in FIG. 4, absorber 24 covers the entire circumference of light conduit 14. This will cause the dark region created by lighthouse 16 to be lengthened slightly. Although this is not normally a problem because the length of absorber 24 is very small compared with the length of light conduit 14, absorber 24 could have slits placed therein in order to allow some of the light to escape thereby eliminating this lengthening of the dark region.

Figure 5:
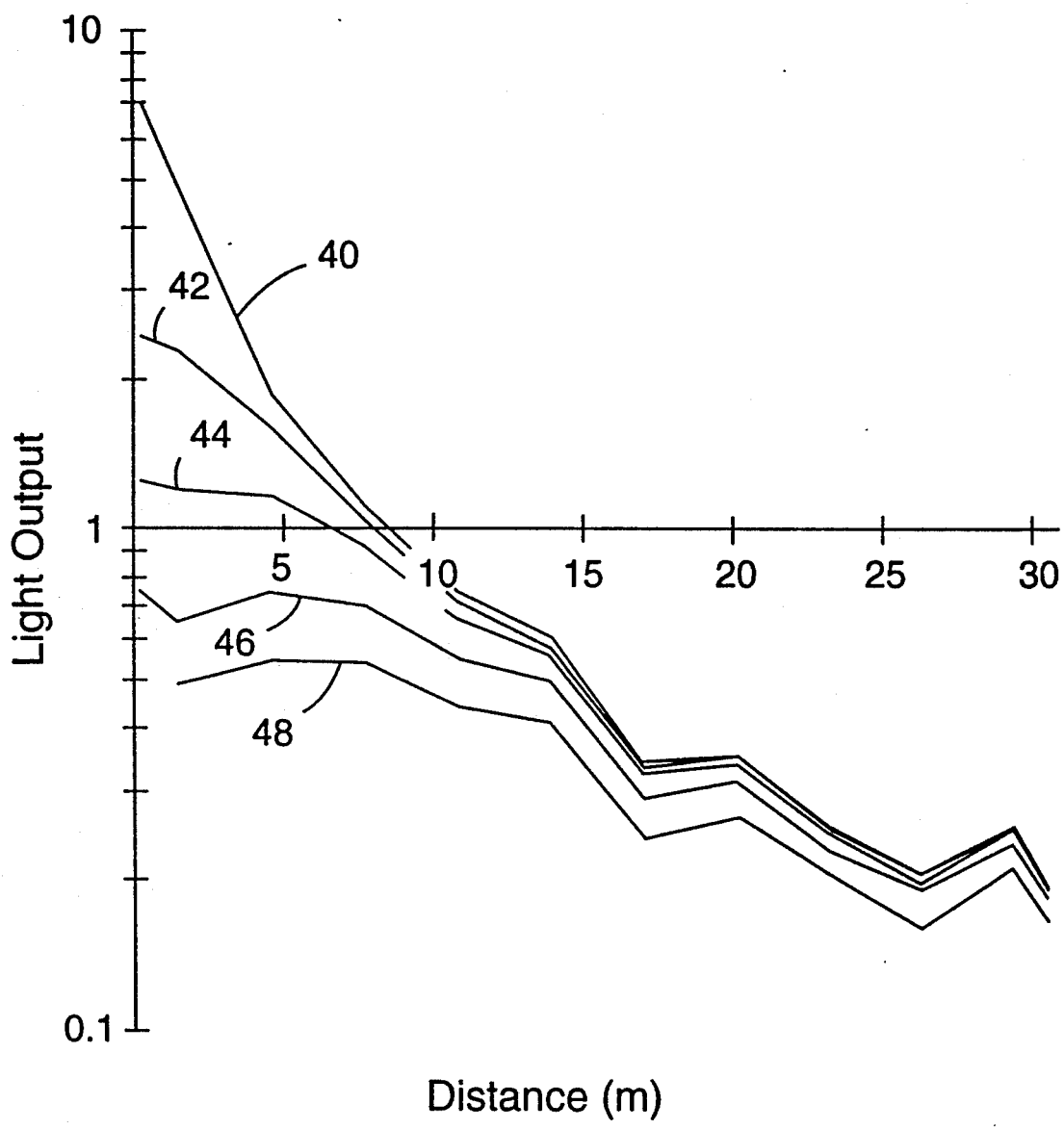
FIG. 5 is a graph showing experimental data comparing the invention to the prior art.

FIG. 5 is a graph of experimental data relating to the invention. In it light output from a linear light source is graphed as a function of distance from the lighthouse along the light conduit. Line 40 of FIG. 5 illustrates the light output according to a line light source according to the prior art. As may be seen, it is significantly brighter for approximately the first five meters of the light conduit than for the remainder. Curves 42, 44, 46, and 48 represent light output having light absorbers of 2.5 cm (1 inch), 7.6 cm (3 inches), 25 cm (10 inches), and 51 cm (20 inches), respectively. As may be seen, even the 2.5 cm absorber significantly reduces the intensity of the bright band near the lighthouse. An absorber as short as 2.5 cm can help linearize the light output of the light source over the first several meters because it absorbs all of the highly uncollimated light that strikes it. Otherwise this light would be conducted along light conduit 14 and be emitted gradually over the first few meters. As further may be seen in FIG. 5, although some improvement in uniformity along the length of the light conduit occurs by continuing to increase the length of the absorber, there is actually very little improvement for absorbers longer than 7.6 cm.

I claim:

1. A line light source comprising:
   a light emitting element capable of providing a partially collimated beam of light;
   a tubular light conduit having an axis and an insertion end, said light emitting element being positioned to emit light into said insertion end; and
   light absorbing means for selectively absorbing light emitted by said light emitting means in a direction that makes greater than a predetermined angle with said axis.

2. The line light source of claim 1 wherein said light absorbing means is cylindrical.

3. The line light source of claim 2 wherein said cylinder is between 1 and 20 inches long.

4. The line light source of claim 3 wherein said cylinder is less than 10 inches long.

5. The line light source of claim 4 wherein said cylinder is approximately 3 inches long.

6. The line light source of claim 1 wherein said light emitting element is enclosed in a housing.

7. The line light source of claim 6 wherein said light absorbing means is in said housing.

8. The line light source of claim 7 wherein said light absorbing means is in said light conduit.

* * * * *